United States Patent [19]

Alfano

[11] Patent Number: 4,479,499
[45] Date of Patent: Oct. 30, 1984

[54] METHOD AND APPARATUS FOR DETECTING THE PRESENCE OF CARIES IN TEETH USING VISIBLE LIGHT

[76] Inventor: Robert R. Alfano, 3777 Independence Ave., Bronx, N.Y. 10463

[21] Appl. No.: 343,874

[22] Filed: Jan. 29, 1982

[51] Int. Cl.³ ............................................. A61B 6/00
[52] U.S. Cl. ..................................... 128/665; 433/29; 356/317; 356/341
[58] Field of Search ................... 128/665; 433/25, 29, 433/32; 356/317, 341

[56] References Cited

U.S. PATENT DOCUMENTS 4,290,433  9/1981  Alfano ................................. 128/665

OTHER PUBLICATIONS

Alfano et al., Journal of Dental Research, vol. 60, Feb., 1981, pp. 120–122.

Primary Examiner—Kyle L. Howell
Assistant Examiner—John C. Hanley
Attorney, Agent, or Firm—Irving M. Kriegsman

[57] ABSTRACT

A method and apparatus for detecting the presence of caries in human teeth using visible light. The tooth is exposed to light of relatively narrow bandwidths. The light from the tooth is preferably examined by two photomultipliers or visually each examining a different wavelength. Caries are detected when the difference in the intensity of the light from the tooth at those two wavelengths changes in a predetermined manner.

2 Claims, 20 Drawing Figures

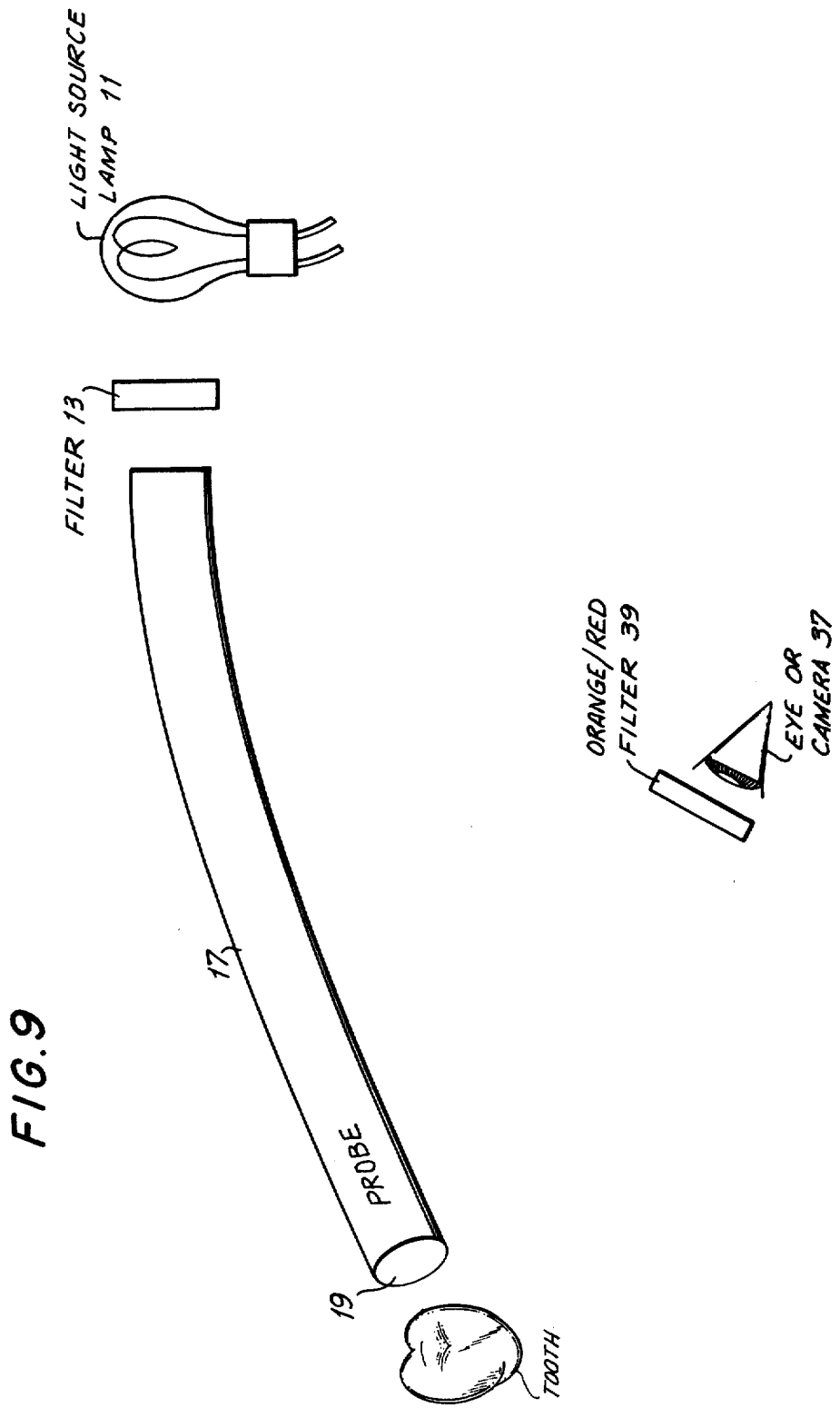

FIG.10A
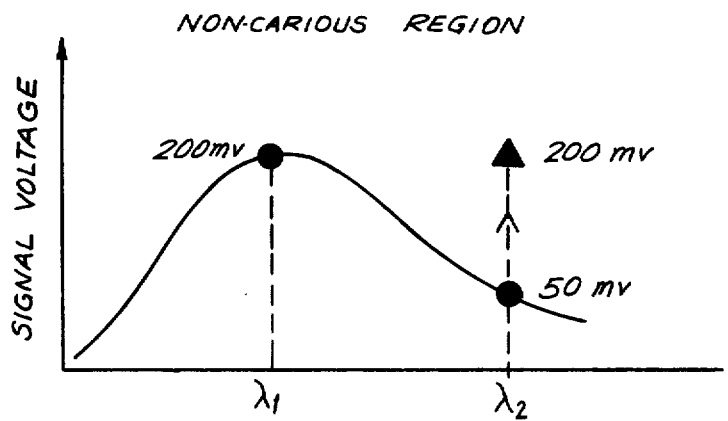
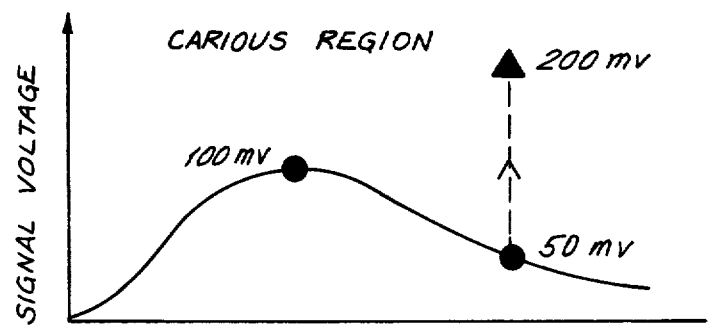
FIG.10B

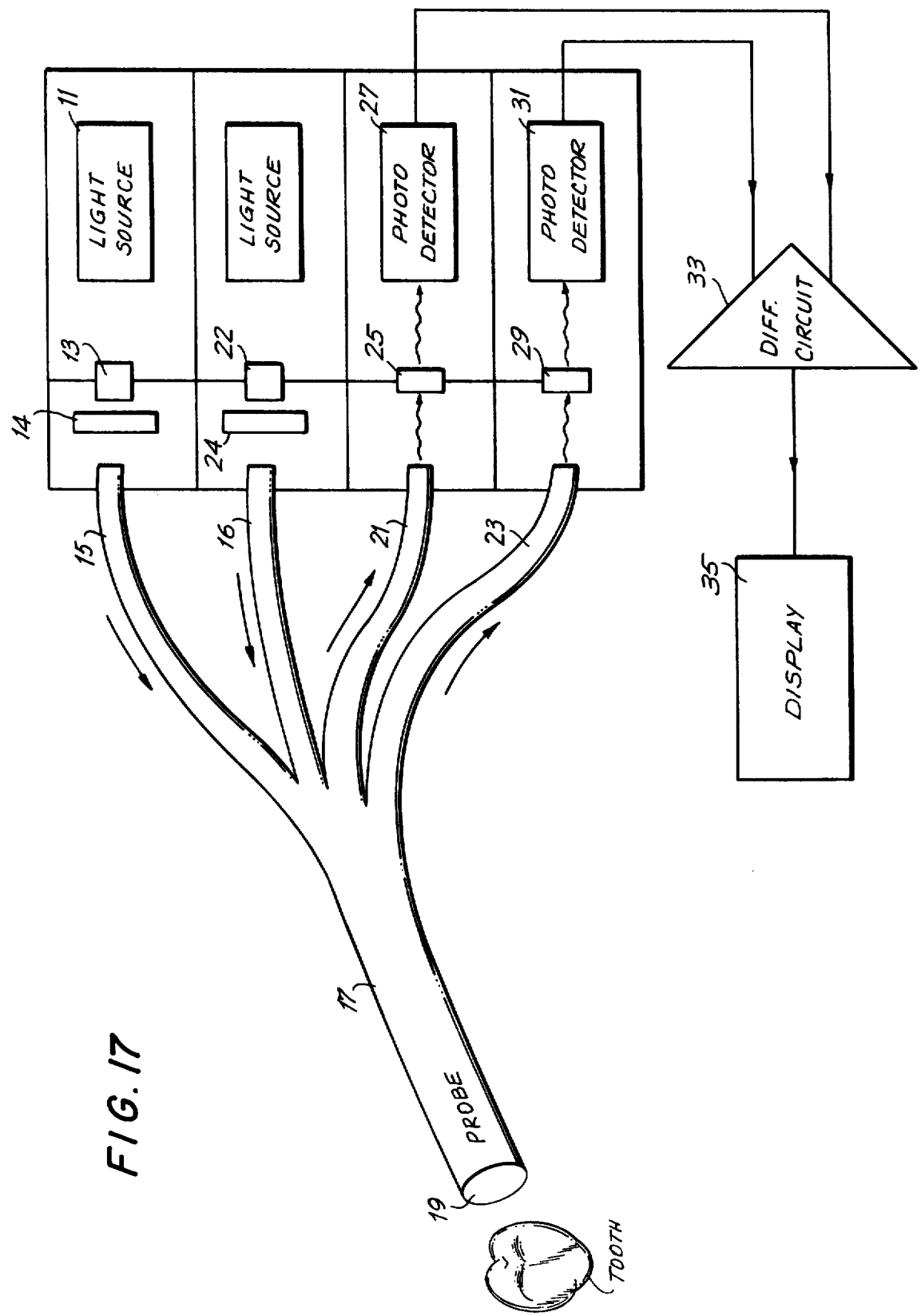

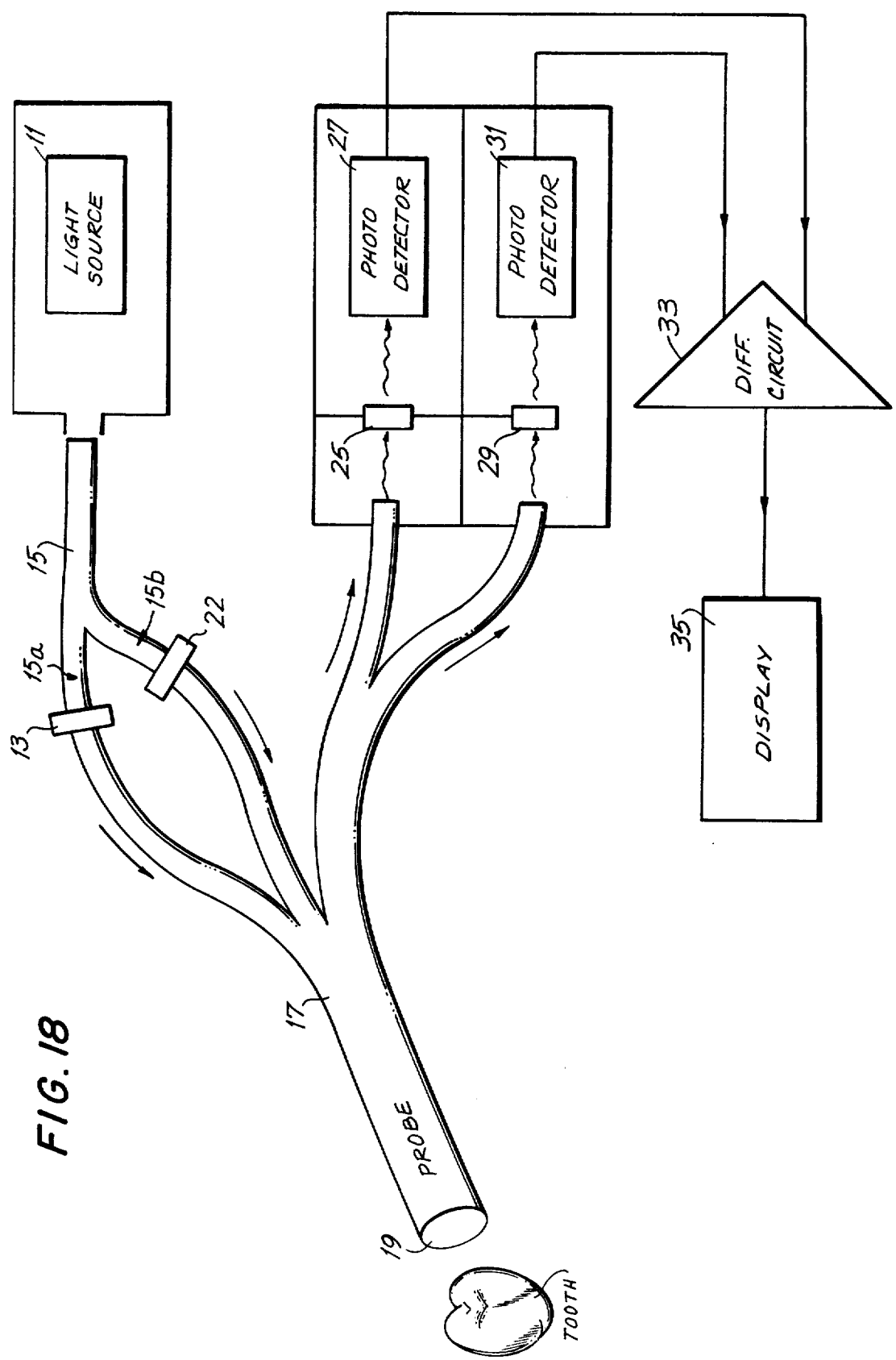

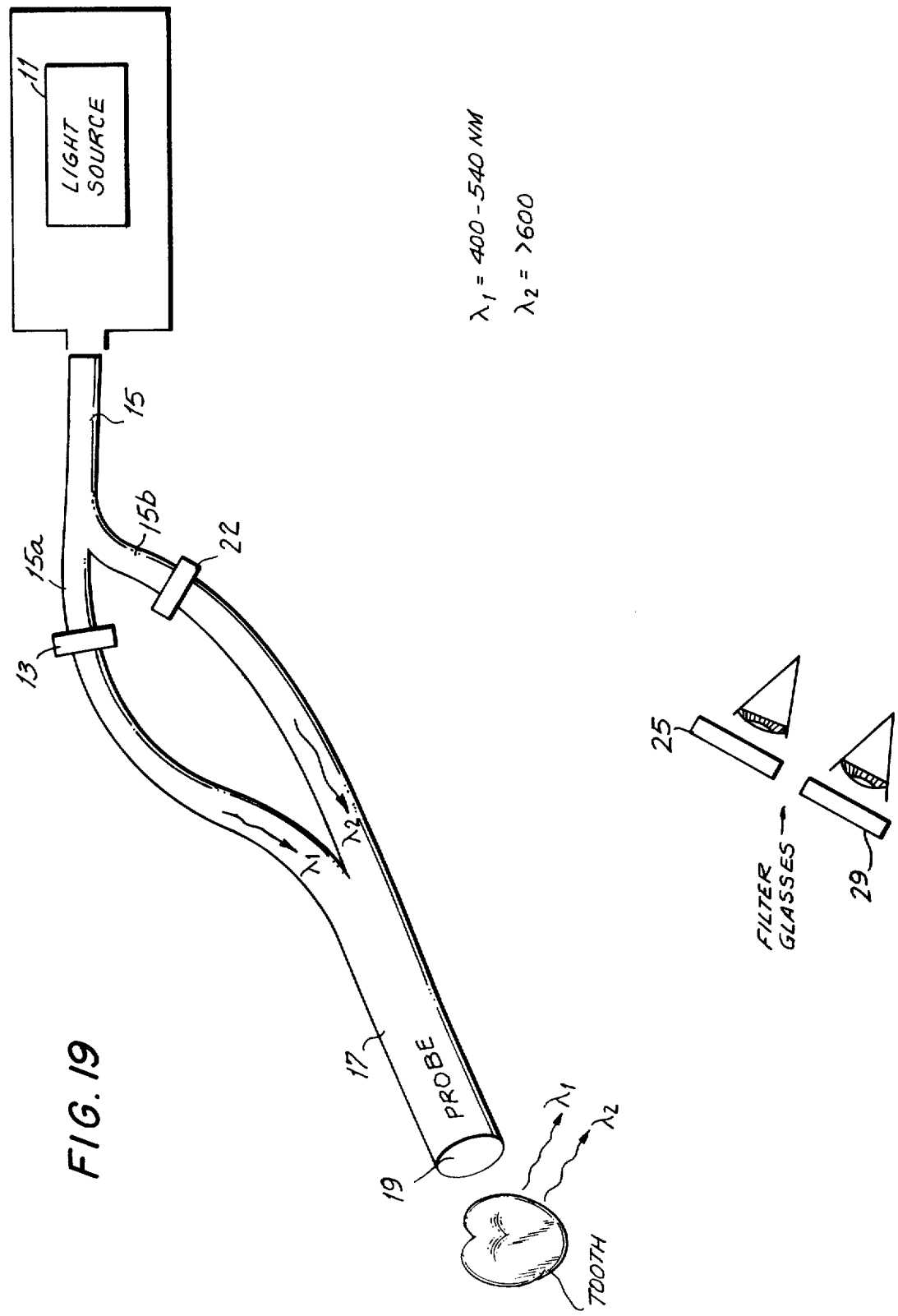

METHOD AND APPARATUS FOR DETECTING THE PRESENCE OF CARIES IN TEETH USING VISIBLE LIGHT

The present invention relates to a method and apparatus for detecting the presence of caries in teeth and more particularly, to a method and apparatus for detecting the presence of caries in the teeth of a person using visible optical diagnostic techniques.

Dental caries or tooth decay is a very common and well known type of desease which, if not properly treated, results in breakdown of the hard structures of the teeth. The progress of tooth decay is gradual, starting slowly from the outside at the enamel and then progressing more rapidly in the dentin. It is believed that dental caries are caused primarily by the action of acid-producing bacteria on certain carbohydrates, principally sugar. If detected, dental decay can be treated by removing the decayed area and filling the resulting cavity with silver amalgam or other inert cavity material. If untreated, dental caries can cause the eventual destruction of the tooth as well as infection or abscess of the jawbone.

In the past, dental caries has been detected by two techniques, one by visual inspection and the other through the use of X-rays.

The problem with visual inspection is that it is not always possible to detect the presence of caries by simply looking at the teeth, especially if the caries is very small or in a very early stage or in an area where it cannot be easily seen. On the other hand, although X-rays have proven to be a very effective manner for detecting the presence of caries and other problems or disorders in the teeth and/or gums, the potentially harmful effects of subjecting people to X-ray radiation has become a matter of great concern over the last several years. In particular, the quantitive relationship between low-dose exposure to X-rays and possible harmful effects, such as cancer, is not clearly shown.

In view of the possible dangerous effects of X-rays, it would appear that a definite need exists for new techniques for detecting the presence of caries and specifically for a technique which can either eliminate or substantially reduce the necessity of X-ray examinations.

Experiments have been conducted in the past which reveal that teeth luminesce when excited by light. In an article by R. L. Hartles and A. G. Leaver appearing in the 1954 Biochemistry Journal, pp. 632,638, the results of certain experiments performed to determine the luminescent properties of teeth when exposed to ultraviolet radiation are discussed at length. Other known articles dealing with the luminescent properties of teeth when exposed to ultraviolet radiation are an article by K. G. Hoerman and S. A. Mancewicz appearing in the 1964 Oral Biology Journal, Volume 9, pp. 517–534 and an article by K. G. Hoerman and S. A. Mancewicz appearing in the 1964 Oral Biology Journal, Volume 9, pp. 535–544.

In U.S. Pat. No. 2,437,916 to W. F. Greenwald there is described a technique for examining living tissue which involves illuminating the tissue with a beam of light and then measuring the intensity of the reflected light at certain wavelength ranges using a phototube and different colored filters.

In U.S. Pat. No. 3,674,008 to C. C. Johnson there is described an instrument which quantitatively measures optical density of a transilluminated body portion. The instrument comprises a controllable, relatively low-frequency oscillator generating pulses which are applied to a light source through a first expand and delay dircuit. A light-conducting source to one side of the body portion and a similar means optically couples another side of the body portion to a light detector. Alternatively, the light source and detector may be placed directly on the body portion. After compensation for ambient light, the output of the detector is coupled to a sample and hold circuit which is triggered by the controllable oscillator through a second expand and delay circuit. The stored signal in the sample and hold circuit is proportional to transmittance and is converted to a visual indication of optical density by a calibrated display means. Methods of using the instrument in diagnosis are discussed, as are further applications to spectrophotometric determinations.

In U.S. Pat. No. 3,963,019 to R. S. Quandt there is described a method and apparatus for detecting changes in body chemistry, for example, glycemia, in which a beam of light is projected into and through the aqueous humor of the patient's eye. An analyzer positioned to detect the beam on its exit from the patient's eye compares the effect the aqueous humor has on said beam against a norm. An excess or deficiency of glucose present in the aqueous humor produces a corresponding positive or negative variation in the exiting beam and thereby indicates a hyper or hypo glycemia condition in the body chemistry of the patent being tested.

In U.S. Pat. No. 4,029,085 to D. P. DeWitt et al there is described a method for determining the bilirubin concentration in the blood serum of a person for measurement of the spectral reflectance of the skin. The disclosed method detects the severity of jaundice, a common neonatal condition, and enables determination of the type of treatment regimen needed to prevent the bilirubin level from becoming sufficiently high to cause kernicterus which can result in brain damage. The method includes measuring the reflectance of the skin within a predetermined frequency spectrum, and more particularly, at a number of specific wavelengths in the visible portion of the spectrum.

In Medical and Biological Engineering, Volume 6, No. 4, August 1968, pp. 409–413, there is described a technique for tissue identification during needle puncture by reflection spectrophotometry.

U.S. Pat. No. 3,709,612 to A. H. Clemens discloses a method and apparatus for examining the color reflectance to determine the pH of liquid samples. The surface is illuminated with polychromatic light and the reflected light is detected at two different wavelengths. One wavelength is employed to stabilize the light output of the light source, the other wavelength is employed to measure a specific color of the surface.

In Anselmo, U.S. Pat. No. 4,170,987 a burn depth diagnosis system illuminates the skin with a broad bandwidth light source. The reflected is split into three beams, filtered into three different wavelengths, and the intensity quantified. The ratio of the intensity of the three beams determine the depth of the burn of the skin.

SUMMARY OF THE INVENTION

It is an object of this invention to provide a new and improved technique for detecting the presence of caries in teeth.

It is another object of the invention to provide a technique for detecting the presence of caries in the teeth which does not involve the use of X-rays.

It is still another object of this invention to provide a technique for detecting the presence of caries in teeth that does not involve the use of other potentially harmful radiation, such as ultraviolet radiation.

It is yet still another object of this invention to provide a technique for detecting the presence of caries in the teeth of a person which is reliable, inexpensive, and easy to use.

It is another object of this invention to provide a technique for detecting the presence of caries in teeth which does not require the use of X-ray sensitive plates or film.

It is still another object of this invention to provide a technique for detecting the presence of caries in teeth which is suitable for visual inspection and using filters or conventional photographic film using optical filters.

It is yet still another object of this invention to provide a technique for detecting the presence of caries in teeth using visible light as source and the teeth's response to that source to probe for caries.

The present invention is based upon the discovery that caries and non-carious regions respond to light relatively differently at different frequencies. For example, in one embodiment of the invention the visible luminescence spectra from caries and non-carious regions of a tooth are substantially different. In particular, the intensity difference between the luminescence of non-carious regions and carious regions changes across the visible spectrum. This embodiment is also based on the further discovery that the relative intensity change of emission from amalgam and metals is smaller than the relative intensity change of emission from caries and that the relative change of the spectrum from adaptic is less than the relative intensity change of non-carious regions. Finally, it has been discovered that the visible luminescence can be achieved using visible light as the excitation source.

The method for detecting the presence of caries according to the teachings of this embodiment involves illuminating a region to be examined with a beam of monochromatic light, measuring the intensity of the visible luminescent radiation at a first wavelength and at a second wavelength where the intensity difference of the luminescence of caries and non-carious regions is different than that difference at the first wavelengths, and then displaying a signal corresponding to the difference. By first determining the magnitude of the difference signal when a region known to be non-carious is illuminated, change in the magnitude of the signal as other regions are examined will indicate the presence of caries.

The apparatus for detecting the presence of caries according to the method includes means for illuminating a region to be examined with a beam of monochromatic light, means for measuring the intensity of the emitted light at the two wavelengths, means for producing a signal corresponding to the difference in the two intensities and means for displaying the difference signal.

The foregoing and other objects and advantages will appear from the description to follow. In the description, reference is made to the accompanying drawing which forms a part thereof, and in which is shown by way of illustration specific embodiments for practicing the invention. These embodiments will be described in sufficient detail to enable those skilled in the art to practice the invention, and it is to be understood that other embodiments may be utilized and the structural changes may be made without departing from the scope of the invention. The following detailed description is therefore, not to be taken in a limiting sense, and the scope of the present invention is best defined by the appended claims.

BRIEF DESCRIPTION OF THE DRAWINGS

The accompanying drawings illustrate various embodiments of the invention according to the best modes so far devised for the practical application of the principles thereof, and in which:

FIG. 9 is a simplified diagram of another embodiment of apparatus for detecting caries by the emission spectra.

FIGS. 10A and B are graph illustrations of the emission spectra of caries and non-carious regions from which Table 1 is in part based;

FIG. 17 is a simplified diagram of an embodiment of apparatus for detecting caries by elastic light scattering.

FIG. 18 is a simplified diagram of another embodiment of apparatus for detecting caries by elastic light scattering.

FIG. 19 is a simplified diagram of another embodiment of apparatus for detecting caries by elastic light scattering.

DETAILED DESCRIPTION

Luminescence Embodiment

Figure 1:
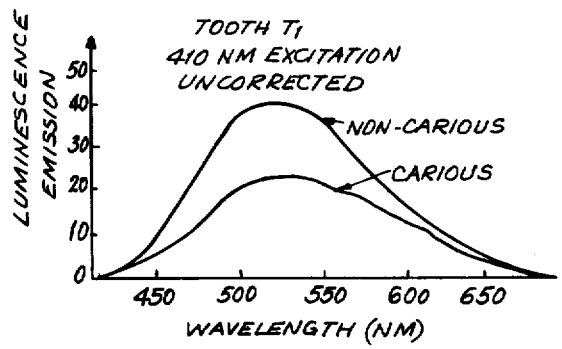
FIG. 1 is a graphical illustration of emission spectra measurements made on a known caries and a non-carious region of a human tooth excited with blue light and a wavelength of 410±5 nm.

Referring now to the drawings, there is shown in FIG. 1 a graph of emission spectrum measurements made on an extracted human tooth $T_1$ excited by blue light at a wavelength 410±5 nm on regions known to be non-decayed and to have caries. Luminescent radiation from the tooth was collected into a SPEX ½-meter scanning spectrometer blazed at 500 nm, second order. An RCA 7265 (S-20) photomultiplier located at the exit of the spectrometer measured the intensity at different wavelengths. The output of the photomultiplier was connected to a lock-in-recorder to display the spectrum. The emission spectra were uncorrected for the spectral response of the system.

Comparison of the curves in FIG. 1 reveals that over the entire spectrum the intensity of the luminescence from non-carious regions is greater than that from the caries. Experiments on various teeth have shown that the total luminescence (the integrated area under the curve) from non-carious regions is 2 to 10 times greater, and possibly as much as 20 times greater, than the luminescence from caries.

The curves also illustrate that the intensity difference between caries and non-carious regions is not constant over the spectrum. In particular, at approximately 480 nm to 600 nm the largest difference in absolute intensity occurs.

Figure 4:
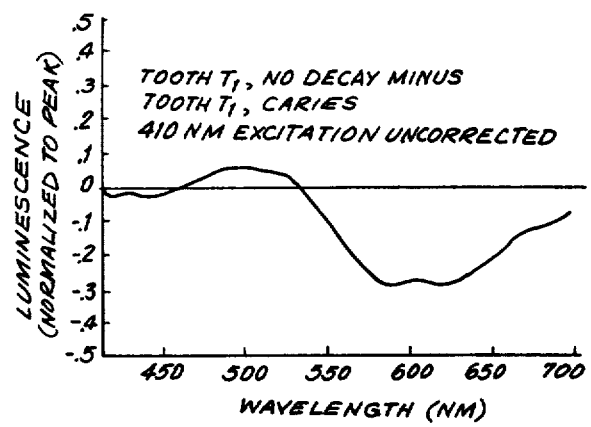
FIG. 4 is a graphical illustration of the difference of the spectra in FIG. 2 and the spectra in FIG. 3.
Figure 2:
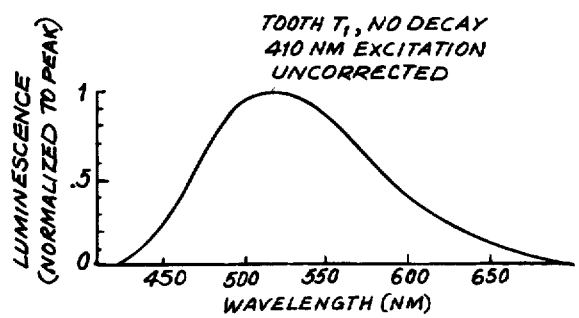
FIG. 2 is a graphical illustration of normalized emission spectra measurements made on the same tooth as in FIG. 1.
Figure 3:
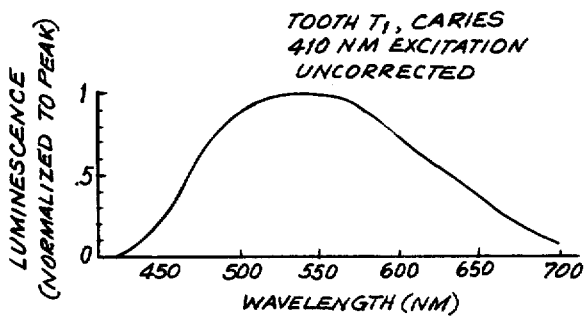
FIG. 3 is a graphical illustration of the normalized emission spectra measurements made on the same tooth as in FIG. 1 at a known carious region.

In FIGS. 2 and 3 the curves of FIG. 1 have been normalized so that the peak of each curve had an arbitrary value of unity. The difference between the curves of FIGS. 2 and 3 is illustrated in FIG. 4. The caries spectra are shifted to the red by about 200 and have relatively more intensity in the longer wavelength region than the spectra obtained from a non-carious region. The largest difference between the spectra from caries and non-carious occurs in the region between 540 and 650 nm with the largest difference occurring at 620 nm. On the other hand, in the region between 450 nm and 500 nm the difference is small. Furthermore, when the normalized spectrum for caries is divided by the normalized spectrum for non-caries, the relative intensity change in the red portion of the spectrum (i.e. 540 to 650 nm) is about two to four times larger than the intensity change in the blue portion of the spectrum. (i.e., 420 to 500 nm).

Figure 5:
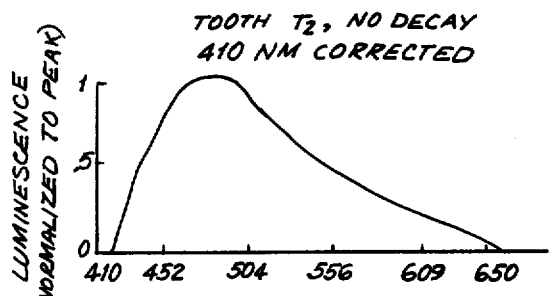
FIGS. 5 and 6 are graphical illustrations similar to FIGS. 3 and 4 respectively but for a different tooth.
Figure 6:
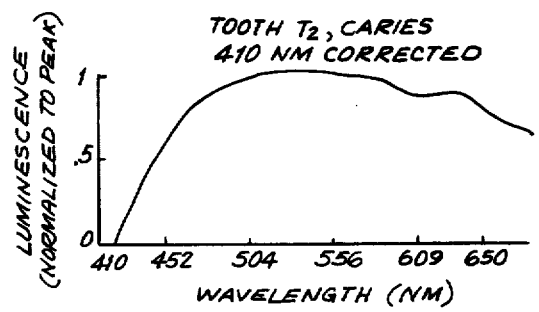

Graphs of the visible emission spectrum measurements for another tooth $T_2$ over a known non-carious regions and a known carious region using the same equipment as above, but being corrected for the spectral response of the detection system are illustrated in FIGS. 5 and 6, respectively.

Figures 7, 8:
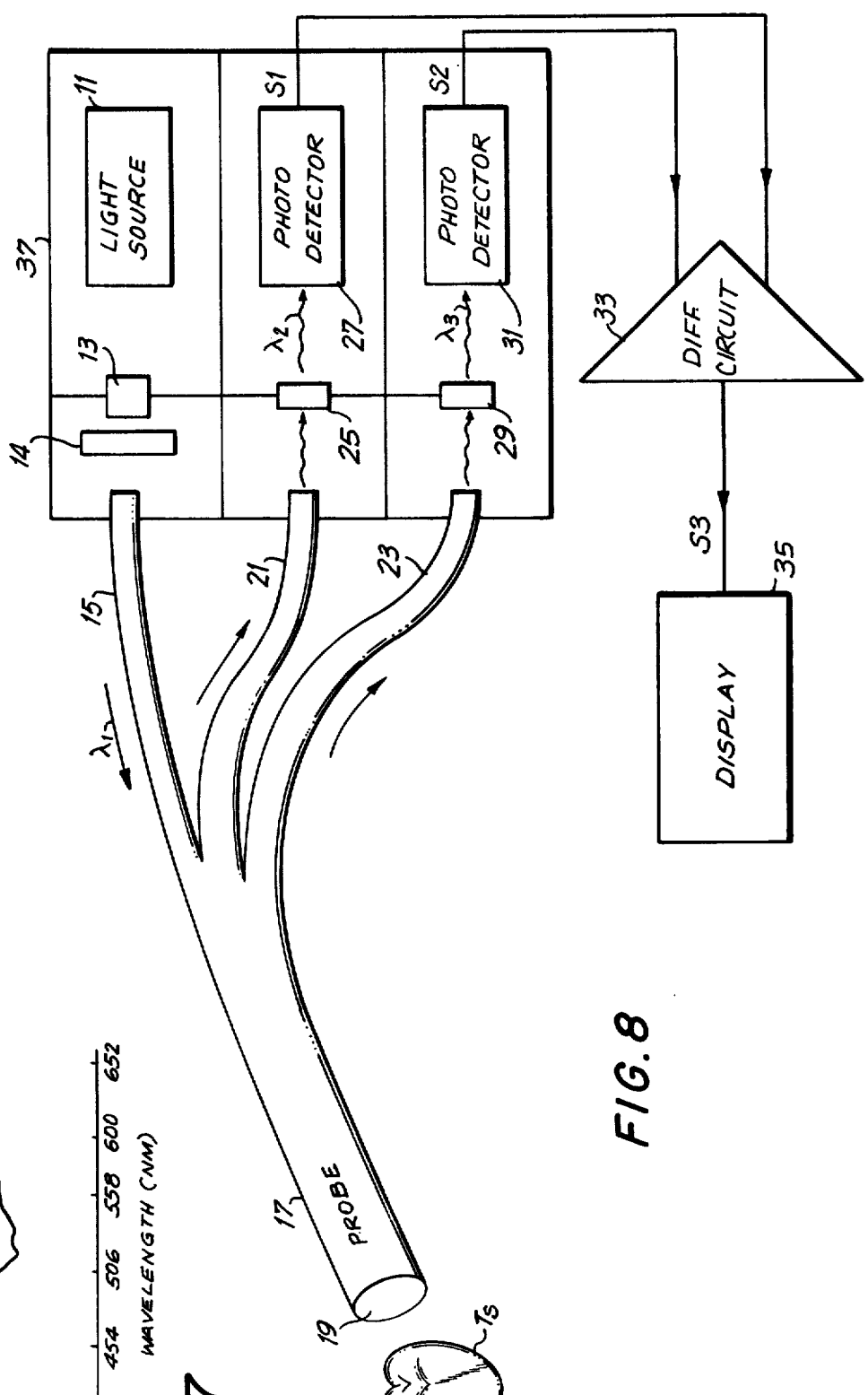
FIG. 7 is a graphical illustration similar to FIG. 4 for the tooth used in FIGS. 5 and 6 but with a light source of 350 nm rather than 410 nm.
FIG. 8 is a simplified diagram of one embodiment of the apparatus for detecting caries by the emission spectra.

A graph of the difference spectra for tooth $T_2$ obtained using the same equipment as used to obtain the graphs in FIGS. 1-4, but with a light source of 350 nm instead of 410 nm is illustrated in FIG. 7.

As can be seen, in each of these cases, in all of which the curves have been normalized, the intensity over a carious region is substantially greater than the intensity for a non-carious region in the red region of the spectrum and in each instance there is an area in the blue region of the spectrum where the difference in decayed and non-decayed region is minimal.

Referring now to FIG. 8 there is illustrated an apparatus for detecting the presence of caries in the teeth of a person according to the teachings of this invention.

The apparatus includes a source 11 of white light, such as a tungsten-halogen filament lamp, and a narrow band filter 13. Alternatively, source 11 may comprise a laser. Light source 11 has power coupled to it from a conventional regulated D.C. power supply (not shown). Narrow band filter 13 has a bandwidth of less than about 30 nm and preferably less than about 10 nm and is designed to pass light at a wavelength $\lambda 1$.

Light from source 11 that is passed by filter 13 is passed through a chopper 14 which removes any ambient light present and is then fed into an input leg 15 of a fiber optic probe 17 may include a lens or lens system (not shown) at the probing end 19 so that non-contact probing may be achieved, facilitating examination of areas between teeth or other areas not easily reachable by direct contact-probing.

Light emerging from output leg 21 is passed through a narrow band filter 25 having a bandwidth of less than about 10 nm and designed to pass light at a wavelength $\lambda 2$ in the visible spectrum and impinges on a photodetector 27. Light emerging from output leg 23 is passed through a narrow band filter 29 having a bandwidth of less than about 10 nm and designed to pass light at a wavelength $\lambda 3$ in the visible spectrum, and impinges on a photodetector 31.

The value $\lambda_2$ depends, at least partially, on the value of $\lambda_1$. For example, if $\lambda_1$ is 410 nm, then $\lambda_2$ may be 450 nm. The value of $\lambda_3$ is also, at least partially, dependent on $\lambda_1$. Thus, if $\lambda_1$ is 410 nm then $\lambda_3$ may be around 610 nm. The value of $\lambda_1$ is any wavelength that will cause teeth to luminesce in the visible spectrum at a wavelength $\lambda_2$. Wavelength $\lambda_1$ is preferably in the visible rather than ultraviolet region to avoid the potential hazards of exposure to ultraviolet radiation. Photodetectors 27 and 31 are conventional photodetectors having maximum sensitivity in the regions of interest, namely at wavelengths $\lambda_2$ and $\lambda_3$, respectively.

Photodetectors 27 and 31 each produce an electrical signal output whose magnitude $S_1$ and $S_2$, respectively, is proportional to the intensity of the incident light. The electrical output signals from photodetectors 27 and 31 are each fed into an electronic circuit 33, such as a differential lock-in amplifier, which is tuned to the frequency and phase of the chopper and which produces an electrical output signal whose magnitude $S_3$ is equal to the differences between the two output signals $S_1$ and $S_2$. Alternatively, electronic circuit 33 may be a differential amplifier turned to the frequency of the chopper 14. Chopper 14 may be eliminated, if the ambient light around the region being probed is not in the area of spectral interest in a darkened room. Still another possibility is to replace photodetectors 21 and 31 with a single photodetector and place a chopper or other device which would direct the light alternately from filters 25 and 29 into the photodetector. Also, the light at $\lambda_1$ and $\lambda_2$ could be chopped different frequencies $w_1$ and $w_2$ directed into one photodetector and the electronic circuit 33 would be tuned to the frequency equal to $w_1 - w_2$.

The output of electronic circuit 33 is connected to a display 35 which may be in the form of a digital or analog meter or a light or buzzer which is activated when difference signal $S_3$ exceeds a predetermined threshold. Display 35 may be mounted directly on fiber optic probe 17.

Light source 11, narrow band filters 13, 25 and 29 and photodetectors 27 and 31 are all situated in a light-tight compartmented housing 37.

In detecting the presence of caries in accordance with the invention, the probe signals $S_1$ and $S_2$ are first determined for a known non-carious region. Any changes in the differences between signals $S_1$ and $S_2$ will indicate that caries are present.

In practice, the probe signals $S_1$ and $S_2$ received from known non-decayed region are preferably balanced and set to zero (i.e., $S_1$–$S_2$ adjusted to zero) so that any relative increase in $S_2$ will produce an unbalanced condition or a voltage signal $S_3$ having a magnitude less than zero. This allows the threshold value for an indicator light or buzzer to be zero. The signals $S_1$ and $S_2$ can be adjusted to zero by any known means such as by adjusting the cathode-dynode voltages of the photodetectors or adding the necessary circuitry to permit adjustment of electronic circuit 31.

Instead of taking the difference between signals $S_1$ and $S_2$, the ratio of signals $S_1$ and $S_2$ may be used to determine the relative change of spectra. This may be achieved by using any conventional type of dividing circuit.

The magnitudes of probe signals $S_1$ and $S_2$ after adjustment to equalize $S_1$ and $S_2$ for a non-decayed area of a human tooth is shown in Table 1, together with the magnitude $S_1$ and $S_2$ from amalgam, from adaptic and from a decayed portion of the same tooth when $\lambda_1$ is 410 nm, $\lambda_2$ is 460 nm and $\lambda_3$ is 600 nm.

TABLE 1

| Tooth Non-Decayed Area | Amalgam | Adaptic | Tooth Decayed Area |
|---|---|---|---|
| $S_1$ = 200 mv | $S_1$ = 2 mv | $S_1$ 200 mv | $S_1$ 100 mv |
| $S_2$ = 200 mv | $S_2$ = 1 mv | $S_2$ 190 mv | $S_2$ 200 mv |

Plotted in FIG. 10A is a curve of the absolute intensity of the output of a photodetector similar to photodetectors 27 and 31 against wavelength when scanning a non-carious region. Similarly, FIG. 10B illustrates the output of a photodetector when scanning caries. As usual the absolute intensity of the curve of FIG. 10B is less than the absolute intensity of curve in FIG. 10A at any particular wavelength. Specifically, at $\lambda_1$ for a non-carious region $S_1$ the output of the photomultiplier has a value of 200 mv and at $\lambda_2$, $S_2$ has a value of 50 mv.

According to the preferred embodiment two photodetectors are used, one to measure $\lambda_1$, photodetector 27, and one to measure $\lambda_2$, photodetector 31. When the cathode-dynodes of photodetector 27 and 31 have the same voltages applied to both, in a non-carious region $S_1$ has a value of 200 mv and $S_2$ has a value of 50 mv. As taught above the values of $S_1$ and $S_2$ for non-carious regions should be adjusted to be identical. This can be effected by increasing the cathode-dynode voltage of photodetector 31 so as to raise the value of $S_2$ from 50 mv to 200 mv, or by a factor of four. This is illustrated in FIG. 10A by the triangle at $\lambda_2$. The same effect could be had by placing an iris in front of a photodetector to reduce or increase intensity or by other well known techniques.

Assuming the adjustments on the photodetectors are set to equalize the values of $S_1$ and $S_2$ in non-carious regions, when caries are scanned the value of $S_2$ will be 200 mv (the triangle in FIG. 10B). However, the value of $S_1$ in FIG. 10B stays at 100 mv.

These results are tabulated in Table 1. Also tabulated in Table 1 are results from amalgam and adaptic, which are not shown in FIG. 10. When the signals $S_1$ and $S_2$ are balanced in a non-carious region, the difference between $S_1$ and $S_2$ is about 1 mv for amalgam, about +10 mv for adaptic, and about −100 mv for a decayed region. Thus, a decayed area can be clearly distinguished from a non-decayed area, from amalgam and from adaptic. It has been found that with a balance accuracy of 1%, caries of about 100 microns can be separated from non-decayed regions with a signal to noise ratio greater than 1. It has also been found that caries 0.01 $cm^2$ in size between teeth can be detected from the scattered light of a 1 $cm^2$ surface.

The intensity spectra can be normalized at any wavelength. However, certain wavelengths will maximize the sensitivity of the apparatus by increasing the difference between $S_1$ and $S_2$ when scanning caries. For example, in the above illustration if the curves were normalized at $S_2$, rather than $S_1$, for non-carious regions $S_1$ and $S_2$ would equal 50 mv. Then, for the caries $S_1$ would be 25 and $S_2$ would remain at 50. The difference, $S_1$–$S_2$, would be only −25 mv. This contrast to a −100 mv when the curves are normalized at the wavelength of $S_1$ for the non-carious region.

In another embodiment of the invention the presence of caries can be detected by exciting a region of the teeth to be examined with a beam of substantially monochromatic light, and visually observing emitted light from the excited region at a wavelength above that of the exciting frequency. This embodiment is illustrated in FIG. 9. In FIG. 9 elements similar to one in FIG. 8 bear like reference numerals. Accordingly, in FIG. 9 there is a substantially monochromatic light source 11. Suitable light souces 11 could be a mercury lamp, a tungsten-halogen lamp, both of which could be used with narrow band pass filters, or argon or cadmium helium lasers. Light from source 11 is directed into fiber optic probe 17 and emerges at probe end 19 to strike the tooth.

The luminescence from the tooth caused by the exciting light from source 11 can be visually viewed either by a human eye or an optical device such as a video or film camera. In FIG. 9 this is shown by the schematic representation of eye 37. Eye 37 views the luminescing tooth through cut-off filter 39. Filter 39 is of the type that passes light above a wavelength and blocks all light having a lower wavelength. For example, if source 11 was a cadmium helium laser which produces light at approximately 440 nm, a suitable filter would be one that transmitted light having wavelengths longer than 470 nm. If source 11 was an argon laser, which produces light at 480 nm, a suitable filter would be one that transmits wavelengths longer than 540 nm.

Because the intensity of the luminescence from caries is less than that from non-carious regions, when viewed through the filter caries will appear as dark spots on the tooth. However so will amalgam and adaptic. A solution to rectify this ambiguity would be to view the tooth through two filters, one passing the green portion of the spectrum and the other passing the red portion of the spectrum. A suitable arrangement might be to make eye glasses, each lens of which would be one of the filters. A comparison of the tooth's luminescence in each portion of the spectrum could be made by blinking the eye. If the decrease in the amount of red light is less than the decrease in the amount of green light when moving from a bright region into a dark region, caries could be suspected. However, if the light transmitted through both filters show about equal decrease in intensity, the dark region might be caused by an amalgam or adaptic.

ELASTIC LIGHT SCATTERING

In another embodiment elastic light scattering can be used to detect caries. Elastic light scattering includes such scattering phenomena as Rayleigh scattering, which has to do with light scattered from the molecular system due to motion fluctuations of the molecules, i.e., rotating entropy fluctuations. Other mechanisms include Mie or Tyndall scattering, which relates to light scattering from large particles such as dust. There is also Brillouin scattering. This effect is caused by thermal disorder of acoustic vibrations in the tooth. Also there may be non-specular reflections and other effects which permit the incident light to escape absorption at the tooth's surface. As used hereinafter elastic light scattering incorporates all of these phenomena.

Figure 11:
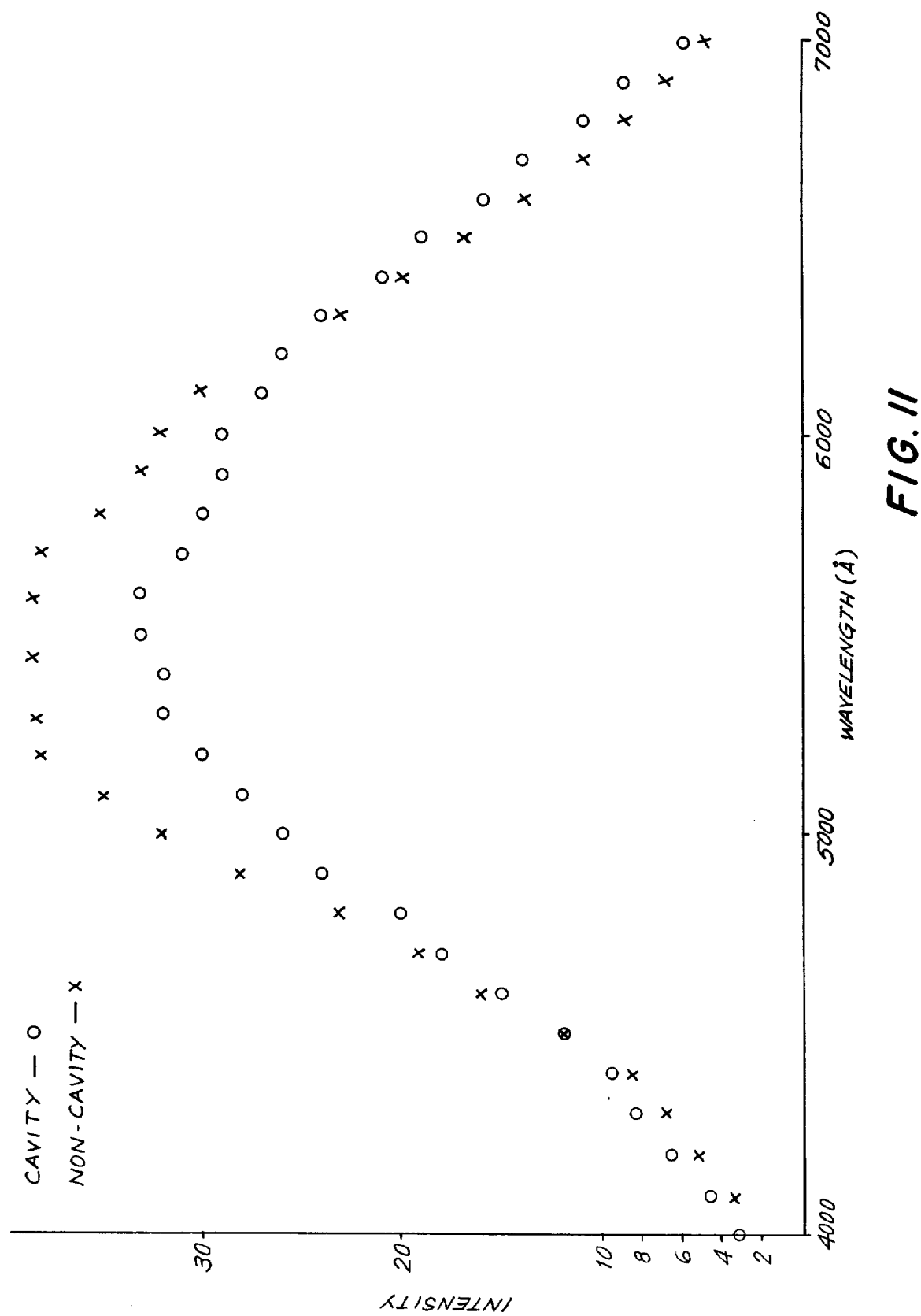
FIG. 11 is a graphical representation of the intensity of the elastic light scattering measured and detected at discrete wavelengths for both caries and non-carious regions.

In FIG. 11 there is shown an intensity curve of light that has been elastically scattered as a function of wavelength in both carious and non-carious regions. Review of these curves reveals that for this particular tooth the non-carious region of a tooth scatters more light than a region with caries in the range between 490 nm and 600 nm. In the range 490 nm and above 630 nm caries and the non-carious regions scatter light substantially identically.

Figure 12:
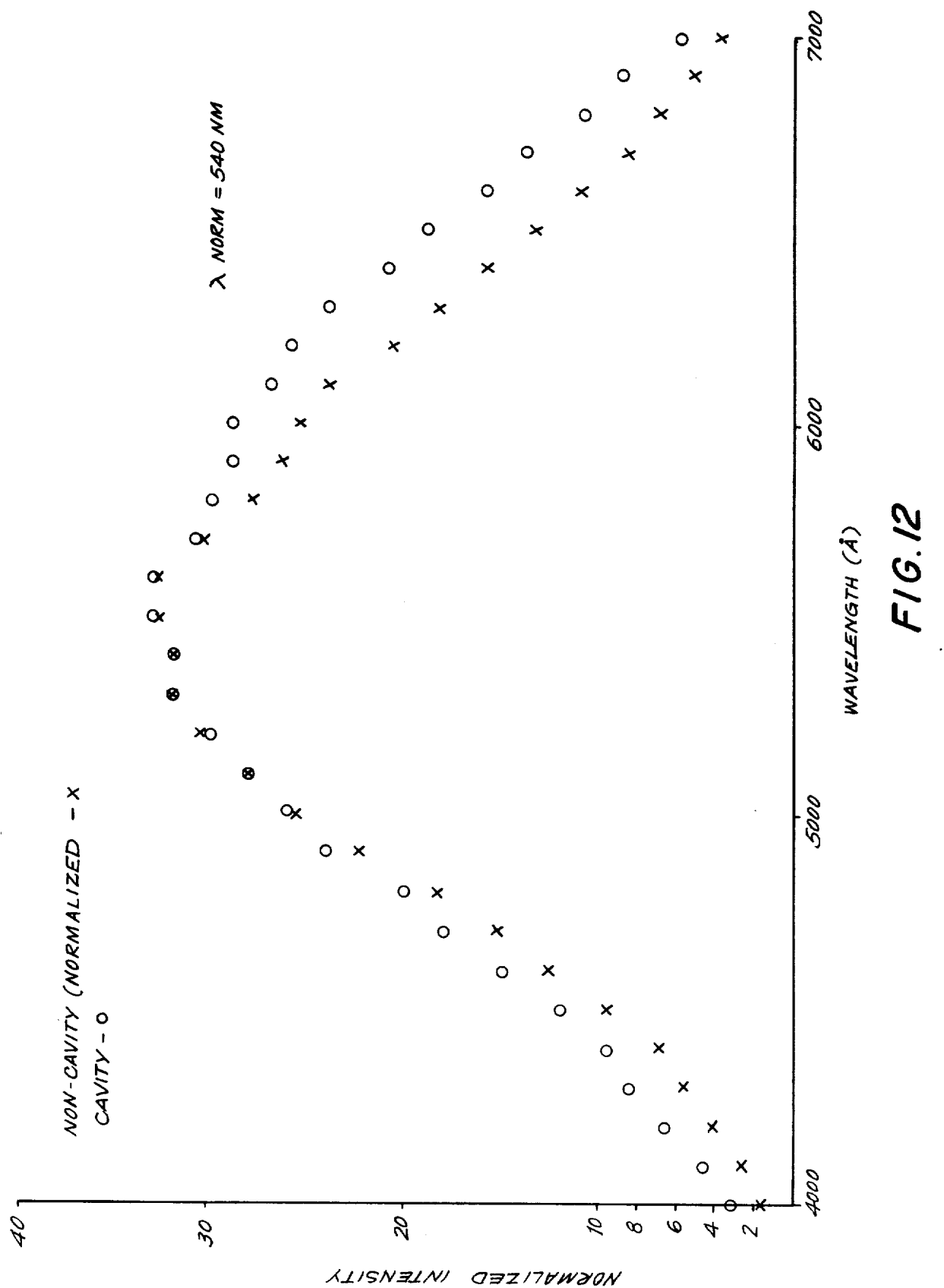
FIG. 12 is the graphical representation of FIG. 11 with the intensity curve of the carious linearly increased (normalized to the peak) so as to have its intensity equal to the intensity of the curve for the non-carious regions at 5400 angstroms.
Figure 13:
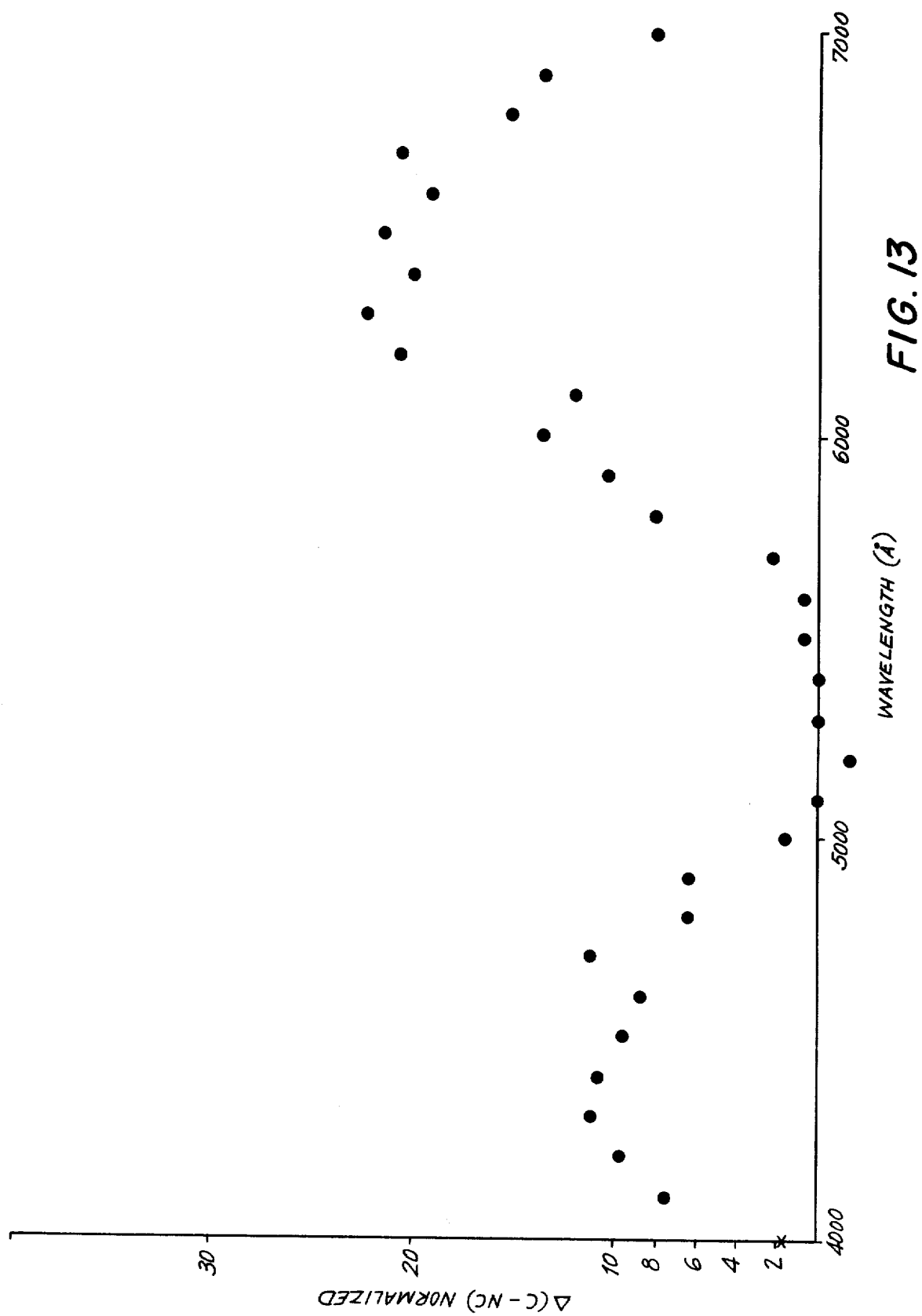
FIG. 13 is a graph of the difference of the two curves illustrated in FIG. 12.

In FIG. 12 the curve in FIG. 11 for the caries has been normalized to have the peak of that curve identical to the peak of the curve for the non-carious region at 540 nm. FIG. 13 plots the differences between the curves of FIG. 12. FIG. 13 reveals that, except for the area in the vicinity of 540 nm the wavelength at which the curves were normalized, a region with caries scatters (relatively) more light than a non-carious region. This is particularly true for light with a wavelength in the neighborhood of 650 nm.

Figure 14:
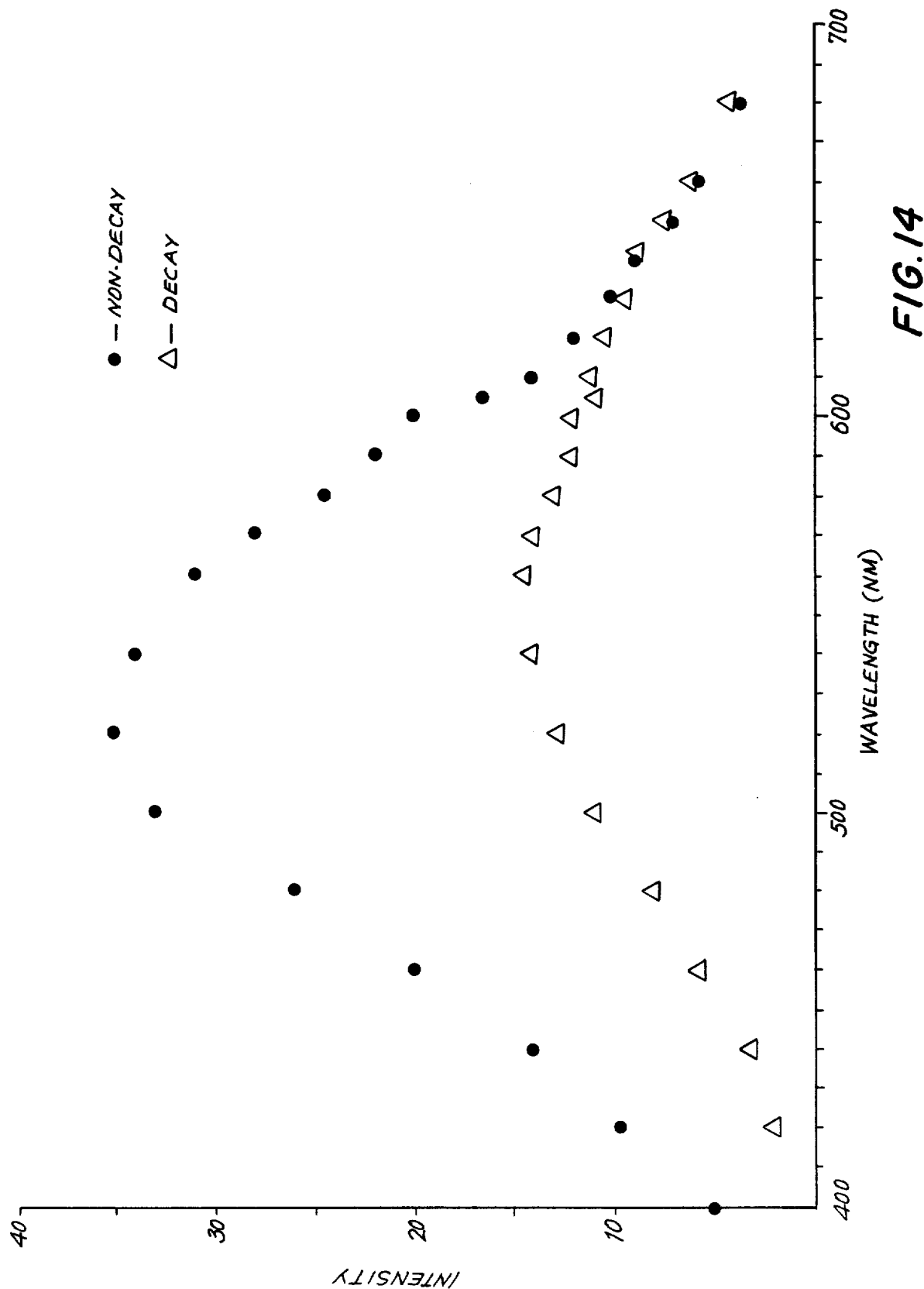
FIG. 14 is a graphical illustration similar to FIG. 11, but for another tooth.
Figure 15:
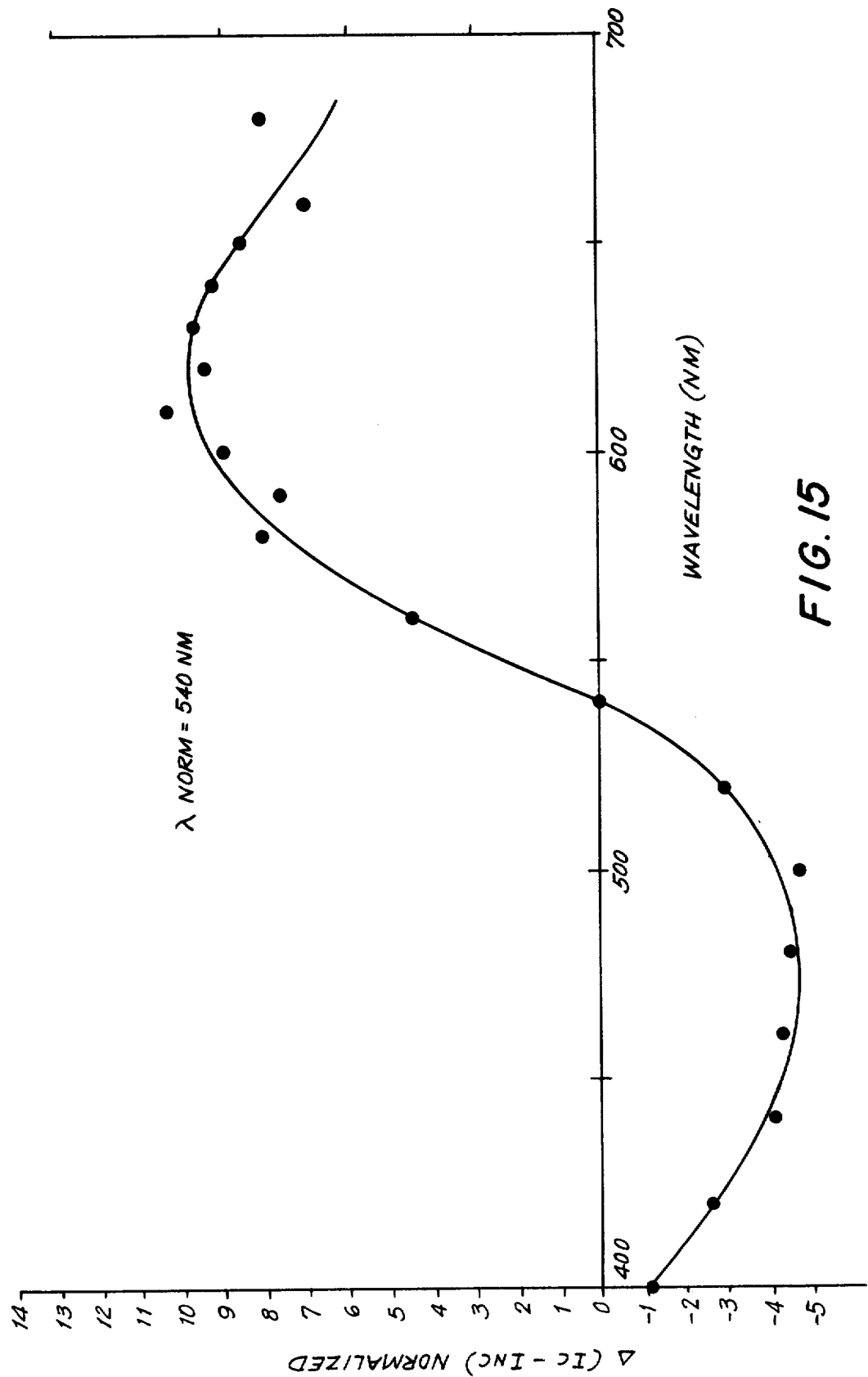
FIG. 15 is a graphical illustration similar to FIG. 13 but for the tooth of FIG. 14, where the curves have been normalized at 5400 angstroms.

FIG. 14 is similar to FIG. 11, but for a different tooth. In this plot the absolute intensity for the light scattered by the non-carious region is much greater than the absolute intensity for that scattered by the region with caries, particularly in the region between 400 nm and 600 nm. Yet, in the region in which the wavelength is greater than approximately 620 nm, the two curves show approximately the same amount of light scattered. The differences may be caused by caries absorbing more light in 400 nm to 600 nm than non-carious spectral region, although the exact physical mechanism is not important to the operation of the invention. FIG. 15 plots the difference between the curves shown in FIG. 14 normalized so that the peak of the curve for caries has been increased to the same value as the intensity of the scattered light from the non-carious regions at a wavelength of 540 nm. Looking at FIG. 15 we again see that there is more light scattered (relatively) from the caries in the 600 nm neighborhood.

Figure 16:
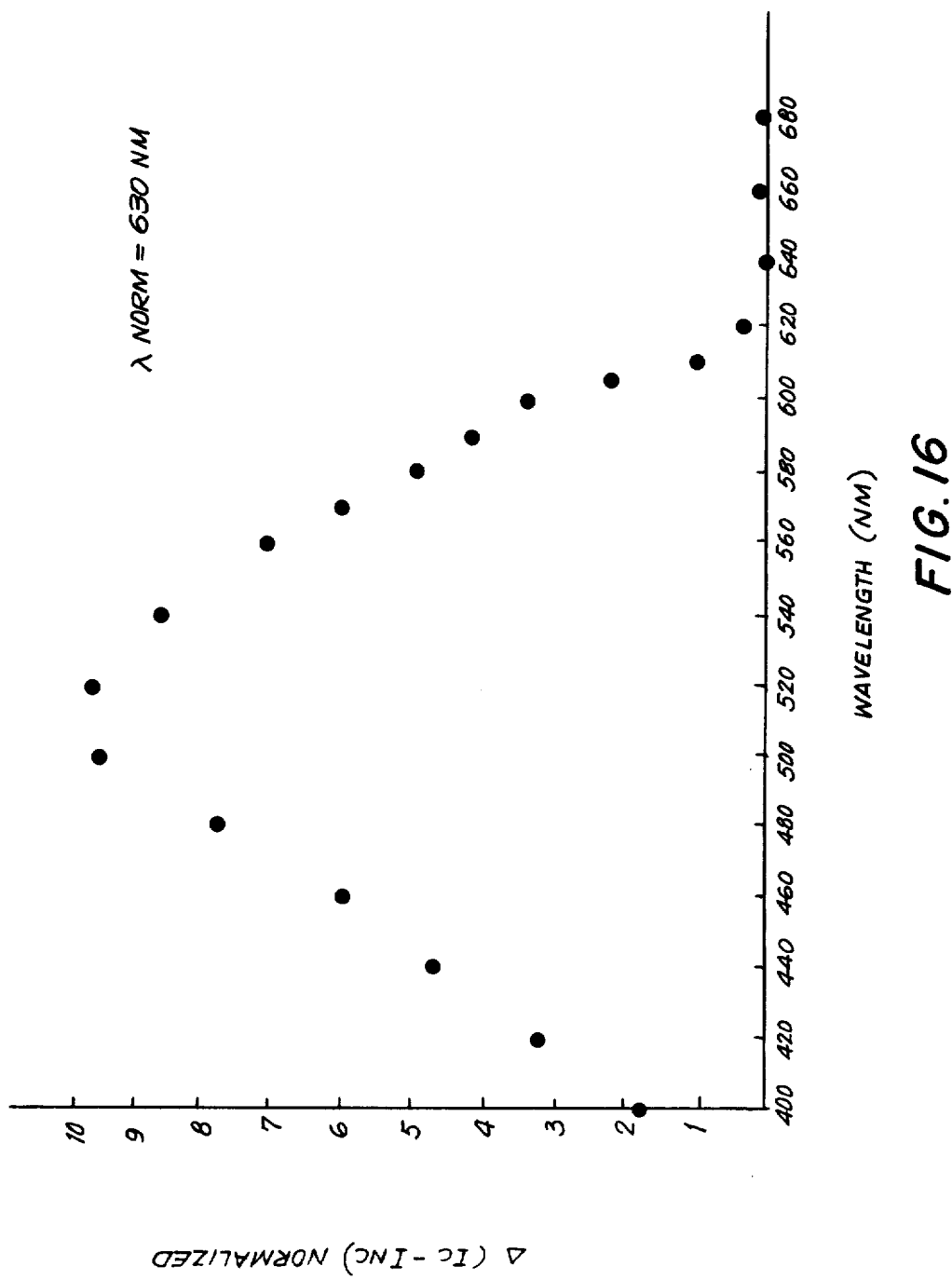
FIG. 16 is a graphical illustration similar to FIG. 15 for the tooth of FIG. 14, but where the caries have been normalized at 6300 angstroms.

FIG. 16 is a plot similar to that shown in FIG. 15, except that the curves of FIG. 14 have been normalized so that the intensities of both curves are equal at 630 nm. FIG. 16 shows a substantial (relative) increase in the light scattering from the non-carious region over the caries below 620 nm.

Referring now to FIG. 17 one embodiment of apparatus to use the above discussed elastic light scattering phenomena is shown. For elements common to this embodiment and the above described embodiments, like reference numbers have been adopted. Light source 11 and a similar light source 12 each have associated therewith a narrow band filter 13 and 22. Light sources 11 and 12 can be as any of the above described monochromatic light sources. In the embodiment of FIG. 17, light sources 11 and 12 can be as any of the above described monochromatic light sources. In the embodiment of FIG. 17, light sources 11 and 12 and filters 13 and 22 produce light of wavelengths of 500 nm and 600 nm, respectively. A polychromatic light source could also be used, but will result in a loss of sensitivity due to fluorescence from other frequencies, spurious signal leakage, other phenomena causing reduction in signal to noise ratios.

As with the prior embodiment, the light is chopped by choppers 14 and 24, respectively, to increase signal to noise ratio at the electronic circuit 33. Input legs 15 and 16 gather the light into fiber optic bundle 17 to emerge at probe 19. From there the light scatters against the tooth, is picked up by probe 19, transmitted by fiber optic bundle 17 through output legs 21 and 23 into filters 25 and 29. Filters 25 and 29 are identical to filters 13 and 22, respectively. Photodetectors 27 and 31 measure the intensity of the light passing through filters 25 and 29 respectively, and produce a signal proportional to the intensity of that light. Those signals are fed to differential amplifier 33 and from there to display 35.

Optimum results are obtained if the wavelengths for filters 13 and 22 are selected to pass wavelengths at which there are large differences in the intensity curves between carious and non-carious regions. For example, referring to FIG. 16, the maximum change of intensity is from the range of 500 nm to 540 nm to the range above 620 nm. Accordingly, one filter, filter 29, should pass any wavelength between 620 nm and 680 nm, and the other filter, filter 25, should pass any wavelengths between 500 to 540 nm.

Operation of this embodiment is similar to that of the embodiment utilizing luminescence. Photodetector 27 and 31 are adjusted to have a zero difference in output signal when a non-carious region is examined. When a region with caries then comes under examination, the signals from photodetectors 27 and 31 will differ in magnitude, and, after processing by differential amplifier 35 which will indicate caries.

FIG. 18 is another embodiment suitable for use with the light scattering phenomena. In this embodiment fiber optic bundle 17 has only one input leg 15. However, input leg 15 splits into two branches, branches 15A and 15B in which are located filters 13 and 22. Thus, only one light source 11 is provided, which produces light at a range of frequencies. In this embodiment light source 11 could be an ordinary tungsten bulb tungsten-halogen lamp, or a dye laser.

Another possible variation would be to substitute for the photodetectors 27 and 31 visual inspection means. For example as in FIG. 19 eyes 37 view the light scattered from the tooth through filters 25 and 29. Caries would be suggested if the light through filter 25 decreases with respect to the light through filter 29.

An embodiment using only one filter passing a frequency band between 480 nm to 600 nm could be used, since the change in scattered light above 600 nm is about the same for caries and non-caries. In this embodiment caries will appear as dark areas.

As one skilled in the art will appreciate, the invention does not involve the use of X-ray radiation and does not require the use of radiation sensitive plates. Furthermore, since the indication of caries is based upon the difference of signals $S_1$ and $S_2$ not merely the intensity of signal $S_2$, any changes in the light emitted scattered or reflected from a region under test, such as may be caused by increasing or decreasing the distance from the probe to the region under test, will not produce a change in the difference. Also, since the excitation radiation is visible light, the tooth or region thereof being examined can readily be observed.

While the invention has been described by specific embodiments and illustrated variations, the present invention is not so limited. Obvious modifications will occur to those skilled in the art. Some of these have been suggested above. Accordingly, the present invention contemplates these modifications and others, without departing from the scope of the invention, as defined by the following claims.

What is claimed is:

1. A method for detecting the presence of caries of the teeth of a person comprising:

radiating a region of the teeth to be examined with light; producing first and second signals corresponding to the intensity of the light scattered at first and second wavelengths, respectively, the intensity of difference of the scattered light between caries and non-carious regions at said first wavelength being measurably different than the intensity difference of the scattered light between caries and non-carious regions at said second wavelength;

producing a third signal corresponding to the difference between said first and second signals;

determining the value of said third signal when a known non-carious region is radiated;

detecting the presence of caries in other regions by said third signal changing from said value in a predetermined manner.

2. A method as in claim 1 including:

selecting said first wavelength in the near neighborhood of the wavelength having the largest intensity of scattered light in non-carious regions;

selecting said second wavelength to maximize the value of said third signal.

* * * * *